United States Patent

Bonelli et al.

[11] Patent Number: 4,732,890
[45] Date of Patent: Mar. 22, 1988

[54] RETRO-INVERSO HEXAPEPTIDE NEUROTENSIN ANALOGS, PROCESS FOR THEIR PREPARATION AND PHARMACEUTICAL COMPOSITIONS CONTAINING THEM

[75] Inventors: Fabio Bonelli; Antonello Pessi, both of Rome; Antonio S. Verdini, Monterotondo, all of Italy

[73] Assignee: Eniricerche S.p.A., San Donato Milanese, Italy

[21] Appl. No.: 893,146

[22] Filed: Aug. 5, 1986

[30] Foreign Application Priority Data

Sep. 19, 1985 [IT] Italy ............................ 22214 A/85

[51] Int. Cl.$^4$ ...................... A61K 37/02; C07K 7/02; C07C 101/24
[52] U.S. Cl. ...................................... 514/11; 530/323; 530/330; 562/561
[58] Field of Search ............... 530/328, 329, 330, 323; 514/11; 562/561

[56] References Cited

U.S. PATENT DOCUMENTS

| | | | |
|---|---|---|---|
| 4,439,360 | 3/1984 | Verdini et al. | 530/330 |
| 4,522,752 | 6/1985 | Sisto et al. | 530/330 |
| 4,560,505 | 12/1985 | Pinori et al. | 530/328 |
| 4,585,586 | 4/1986 | Di Trapani et al. | 530/328 |
| 4,638,046 | 1/1987 | Verdini et al. | 530/329 |

Primary Examiner—Delbert R. Phillips
Attorney, Agent, or Firm—Oblon, Fisher, Spivak, McClelland & Maier

[57] ABSTRACT

Hexapeptides with vasodilating and hypotensive activity are described corresponding to the formula:

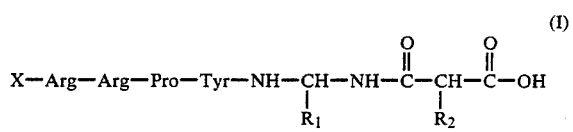

wherein:
X is a hydrogen atom or an acyl radical $R_3$-CO- wherein $R_3$ is a straight or branched ($C_1$-$C_7$)alkyl group,
$R_1$ and $R_2$, each independently, represent the side-chain residue of the amino acid glycine (—H), alanine (—$CH_3$), valine

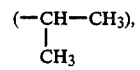

leucine

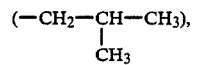

or isoleucine

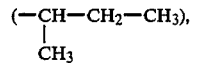

Arg is the abbreviated designation for arginine, Pro is the abbreviated designation for proline, Tyr is the abbreviated designation for tyrosine, and the pharmaceutically acceptable salts, lower alkyl esters and amides thereof, a process for their preparation and the pharmaceutical compositions containing them.

5 Claims, No Drawings

RETRO-INVERSO HEXAPEPTIDE NEUROTENSIN ANALOGS, PROCESS FOR THEIR PREPARATION AND PHARMACEUTICAL COMPOSITIONS CONTAINING THEM

The present invention relates to retro-inverso hexapeptide neurotensin analogs with vasodilating and hypotensive activity, a process for preparing them, intermediates used in the process, and pharmaceutical compositions containing them.

More particularly, as a first object, this invention concerns retro-inverso hexapeptide neurotensin analogs corresponding to the following general formula:

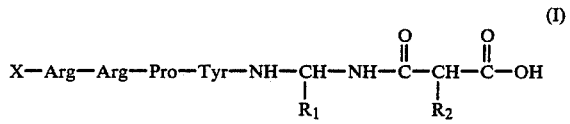

wherein:

X is a hydrogen atom or an acyl radical $R_3$—CO— wherein $R_3$ is a straight or branched ($C_1$-$C_7$)alkyl group, $R_1$ and $R_2$, each independently, represent the sidechain residue of the amino acid glycine (—H), alanine (—$CH_3$), valine

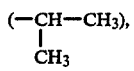

leucine

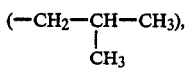

or isoleucine

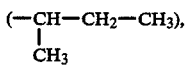

Arg is the abbreviated designation for arginine,
Pro is the abbreviated designation for proline and
Tyr is the abbreviated designation for tyrosine; their corresponding pharmaceutically acceptable salts, lower alkyl esters and amides.

The term "lower alkyl" when used in the instant application is intended to represent those alkyl groups either straight or branched chain, which have from 1 to 5 carbon atoms. Examples of such alkyl groups are methyl, ethyl, propyl, iso-propyl, butyl, sec-butyl, pentyl and the like.

Pharmaceutically acceptable salts are salts of the compounds of formula (I) with various organic and inorganic acids and bases. Such salts, which may be obtained either directly from the process of this invention or by reacting the peptide with one or more equivalents of the appropriate base or acid in a solvent or medium wherein the salt is insoluble or in a solvent which is then easily removed, include ammonium salts, alkali metal and alkaline earth metal salts such as sodium, potassium, calcium and magnesium salts, salts with organic bases e.g. N-methyl-D-glucamine and dicyclohexylamine, and the like; also acid addition salts with organic or inorganic acids such as HCl, HBr, $H_2SO_4$, $H_3PO_4$, sulphonic acids, carboxylic acids such as acetic acid, oxalic acid, pivalic acid, and the like.

It should be noted that the peptides of formula (I) above have at least two basic nitrogens giving rise to addition salts with one to possibly two equivalents of acid. If desired, a particular acid addition salt is converted into another acid addition salt by treatment with the appropriate ion exchange resin in the manner described by R. A. Boissonas, et al., Helv. Chim. Acta, 43, 1349 (1960). While the non-toxic physiologically acceptable salts are preferred, other salts may also be useful e.g. in isolating or purifying the product.

Unless otherwise specifically indicated, the amino acids Arg, Pro, and Tyr in the compounds of formula (I) above have absolute configuration L-.

Neurotensin (NT), is a natural tridecapeptide of nervous and intestinal origin, whose sequence is pGlu-Leu-Tyr-Glu-Asn-Lys-Pro-Arg-Arg-Pro-Tyr-Ile-Leu-OH.

It was originally isolated from bovine hypothalamus (see R. Carraway and S. E. Leeman, J. Biol. Chem., 248, 6854 (1978)) and, following its characterization (J. Biol. Chem., 250, 1907 (1975)), thoroughly investigated showing a wide spectrum of pharmacologic actions.

In particular, NT shows multiple effects on the mammalian cardiovascular system, the most relevant ones being:

production of hypotension in the rat, rabbit, pig, goat, and dog;

change in heart rate;

increase in vascular permeability and vasodilation in the rat;

positive inotropic and chronotropic effects in the isolated atria in the rat and guinea pig;

vasocostriction in the adipose tissue in the dog, in the perfused heart and isolated portal vein in the rat, and vasodilation in the dog intestine.

Although a specific role of the various cardiovascular effects elicited by NT, particularly in humans, remains to be established, the interaction between NT and the cardiovascular system necessarily has remarkable physiological and/or pathological implications.

NT, which is active on the cardiovascular system in a variety of animal models at relatively low dosages (50-1000 $\mu$mol), is therefore a compound of particular interest for the treatment of hypertension.

However, in vivo experiments in rats have shown that NT biological activity rapidly declines with a halflife of about 0.5 min.

The reason for such decrease in in vivo biological activity is the presence in the molecular structure of specific sites where the peptide bond is hydrolysed by peptidase enzymes. The hydrolytic action of these enzymes breaks up the molecule in fragments which are devoid of biological activity or have a biological activity which is lower than NT itself.

The specific sites for enzymatic hydrolysis as well as NT main metabolites have been elucidated by means of specific RIA analyses.

It has been found that the peptide bonds which are most susceptible to enzymatic hydrolysis are $Arg^8$-$Arg^9$ and $Tyr^{11}$-$Ile^{12}$.

Other sites at which degradation may preferentially occur are the $Ile^{12}$-$Leu^{13}$ peptide bond by carboxypeptidase, the $Glp^1$-$Leu^2$ bond by L-pyroglutamyl-hydrolase and the $Tyr^3$-$Glu^4$ bond by chymotrypsin.

Furthermore it has been observed that the $NT^{1-11}$ fragment obtained through hydrolysis of the $Tyr^{11}$-

Ile[12] peptide bond, is further hydrolyzed by a specific enzyme which liberates the C-terminal tyrosine residue (R. E. Carraway, in "Neurotensin, a Brain and Gastrointestinal Peptide", Ed. C. B. Nemeroff and A. J. Prange, Ir., The New York Academy of Sciences, New York, 1982, p. 17).

Therefore, synthesis of neurotensin or a derivative thereof with a longer-lasting in vivo biological activity is one of the goals presently facing the researchers involved in this field.

According to Italian patent application 21080 A/83, neurotensin analogs are prepared wherein the Ile[12]-Leu[13] peptide bond is inverted.

The reversal of the direction of this bond affords a molecule which is more resistant towards peptidases thus prolonging its in vivo biological activity.

It has been found also that, owing to an induced conformational change effect, this reversal enhances also the stability of the peptide bond linking the amino acids at positions 11 and 12.

These NT analogs however still maintain the NT undesired biphasic effect. It has been observed in fact that the hypotensive effect elicited in vivo is followed soon by a hypertensive effect.

Therefore a further goal is the synthesis of neurotensin analogs free from said side-effect.

Structure-activity studies with various fragments obtained through NT enzymatic hydrolysis showed that the C-terminal hexapeptide whose amino acid sequence is Arg-Arg-Pro-Tyr-Ile-Leu contains all the necessary information for eliciting a biological response.

However it has been observed that the C-terminal hexapeptide has an in vivo biological activity much lower than NT itself. This fact strongly limits the therapeutical use of said hexapeptide.

It has now surprisingly been found that the retro-inverso NT-(8-13) hexapeptide derivatives of formula (I) while sharing a hypotensive and vasodilating activity comparable to NT are free from the disadvantages of the natural product.

These compounds in fact show a hypotensive activity comparable to but lasting longer than NT; furthermore, unlike NT, they do not elicit any re-bound hyptertensive effect.

More particularly the results obtained in representative experiments carried out with the compound of Example 1 are reported in following Table I.

Typically, male rats weighing about 200-300 g, anesthetized with urethane (1.75 g/Kg i.p.), were employed in these tests and the hexapeptide

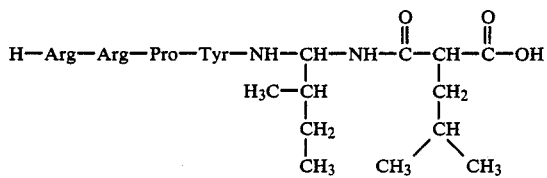

was administered by i.v. injection in the right femoral vein at a dosage of 20 meq/Kg body weight.

Blood pressure was recorded at different times following the injection.

The basal values were on the average 80-130 mmHg.

TABLE I

| Time from admin. | Arterial pressure (mmHg) | Pressure Δ |
|---|---|---|
| 30' | 80-125 | 0-5 |
| 1 h | 75-125 | 5-5 |
| 2 h | 75-125 | 5-5 |
| 2.5 h | 75-120 | 5-10 |
| 3.5 h | 75-120 | 5-10 |
| 4.5 h | 70-110 | 10-20 |
| 5 h | 70-110 | 10-20 |
| 6 h | 65-105 | 15-25 |

A further object of the present invention is therefore the use of said hexapeptides in the therapy of hypertension and other related clinical conditions. To this purposes the compounds of the present invention may be formulated in solid or liquid dosage forms such as tablets, capsules or elixirs for oral administration, or sterile solutions or suspensions for intravenous or intramuscular administration.

It is apparent to any skilled person that the daily dosage to be administered to patients in need of such treatment to provide optimal pharmacuetical efficacy will vary from patient to patient depending upon the nature and severity of the disease, the patient's weight, the route of administration and other possible concurrent medical treatment.

A still further object of the present invention is therefore a pharmaceutical composition comprising a therapeutically effective amount of the retro-inverso hexapeptide of formula (I) or a pharmaceutically acceptable salt, lower alkyl ester or amide thereof in a pharmaceutically acceptable liquid or solid carrier. In addition to the carrier and the active principle, said pharmaceutical composition may also contain the conventional additives, such as stabilizers, binders, lubricants, flavoring agents and the like.

The proportion of the active principle is determined by its solubility in the given carrier, by the given carrier, by the route of administration choosen and by standard pharmaceutical practice. The amount of active principle contained in a unit dosage form is such that a suitable schedule of treatment in the dosage range indicated above can be applied.

The compounds of formula (I) are readily prepared by using the solid phase sequential synthesis technique which comprises (a) covalently bonding a dipeptide (II)

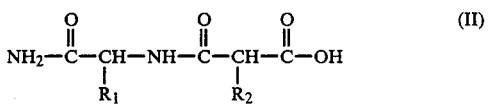

wherein $R_1$ and $R_2$ are as defined above, to an activated resin support (b) converting the carbamyl group of the resin-bound dipeptide (II) to amino by reaction with [1,1-bis(trifluoroacetoxy)iodo]benzene (TIB), (c) stepwise assembling the hexapeptide (I)

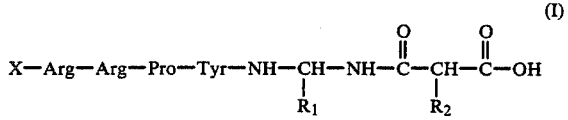

wherein X, $R_1$ and $R_2$ have the same meanings as above, by sequentially coupling the individual amino acids to the resin-bound dipeptide obtained in step (b), (d) cleaving the thus obtained hexapeptide from the resin support and recovering it, and (e) purifying the obtained hexapeptide (I) by chromatography.

More particularly, the dipeptide of formula (II) is covalently bonded to an insoluble polymeric resin support activated through reaction with an appropriate peptide-resin linkage agent. The polymeric support is any of the polyamide supports conventionally used in solid-phase peptide synthesis. According to a preferred embodiment, said support is a polydimethylacrylamide-based resin such as those developed by E. Atherton et al. (J. Am. Chem. Soc., 1975, 97, 6585) or by Arshady et al. (J. Chem. Soc., Perkin Trans. I, (1981), pp. 529–536) suitably functionalized with primary amino groups which provide appropriate linkage points for the growing peptide. These groups are in fact amidated by reaction with a suitable benzyl alcohol derivative and the dipeptide (II) is then attached to the resin through ester bond formation with the hydroxy group of the peptide-resin linkage agent, in the presence of a condensing agent. Suitable condensing agents are widely known in the art, however, according to a preferred embodiment, esterification of the dipeptide of formula (II) to the resin is carried out in the presence of 4-dimethylaminopyridine which is known to be a particularly effective catalyst for ester bond formation under mild conditions. In this step the dipeptide (II) is used as an activated ester thereof, preferably as the corresponding benzotriazolyl ester. According to a conventional procedure, said activated ester is easily prepared by contacting the dipeptide (II) with an equimolar amount or a slight molar excess of 1-hydroxybenzotriazole (HOBT) and a substantially molar equivalent of dicyclohexylcarbodiimide (DCCI) in an inert organic solvent, preferably methylene chloride, tetrahydrofuran or dimethylformamide. The mixture is kept at $-20°$ C. to $10°$ C., preferably at $0°$ C., from 15 minutes to 2 hours, then the thus obtained activated ester is filtered directly into the reaction vessel containing the functionalized resin, the esterification catalyst (DMAP) and an equimolar amount of a nitrogen containing tertiary organic base such as N-methylmorpholine (NMM) or N-ethylmorpholine (NEM) which acts as the acid accepting agent. The esterification reaction which is conveniently carried out at room temperature is generally complete in a few hours.

The subsequent conversion of the resin-bound amide into amine with TIB is performed in mixed aqueous organic media according to the teachings of EP-A-97994 and EP-A-127234 which are incorporated herein by reference.

The synthesis is then brought to completion according to the usual methods employed in solid-phase peptide synthesis which consists in assembling the desired peptide sequence by the stepwise addition of the individual suitably protected amino acids to the thus obtained polymer-bound amine, up to completion of the synthesis.

Coupling reactions are preferably carried out using pre-formed symmetrical anhydrides where the amino groups are suitably protected as the corresponding fluorenylmethoxycarbonyl (Fmoc) derivatives. Thus, prior activation of the N-fluorenylmethoxycarbonyl-amino acid with 0.5 equivalents of dicyclohexylcarbodiimide (DCCI) in the presence of a polar aprotic organic solvent, e.g. a halogenated hydrocarbon, is preferably employed, with isolation of the resulting symmetrical anhydride by filtration from precipitated dicyclohexylurea (DCU), evaporation of the filtrate and dissolution in dimethylformamide (DMF) before its addition to the resin. Preferred side-chain protecting groups for the OH group of tyrosine and the guanidino group of arginine are tert-butyl or tert-amyl and substituted phenylsulphonyl groups respectively. Intermediate Fmoc-peptide resins are conveniently deprotected with 20% piperidine in dimethylformamide following a standard procedure (see E. Atherton et al., J. Chem. Soc., Perkin Trans. I, 1981, p. 538 et seq.).

At the end of the synthesis the hexapeptide is cleaved from the resin support by treatment with a 6% solution of thioanisole in trifluoroacetic acid.

This treatment allows the simultaneous cleavage of all the side-chain protecting groups. Cleavage of the synthesized hexapeptide proceeds with a yield, calculated by amino acid analysis of the residual resin, which is higher than 90%.

The thus obtained hexapeptides are then purified by chromatography, typically on a ion-exchange resin. The identity of the products is confirmed by NMR.

Purity of the hexapeptides (I) is confirmed by reverse phase-HPLC. The dipeptide of formula (II) which is employed as the starting material in the process of the present invention may be easily prepared by homogeneous phase condensation of a suitably selected amino acid amide of formula (III) and a malonyl derivative of formula (IV)

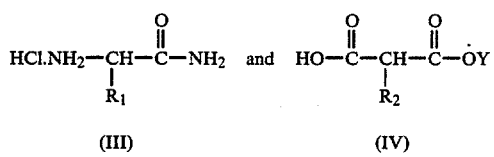

wherein Y is methyl, ethyl, benzyl or t-butyl.

The condensation reaction is carried out in the presence of an inlet organic solvent and a condensing agent selected among those known in peptide synthesis.

Suitable solvents are selected from halogenated hydrocarbons, e.g. methylene chloride, lower alkyl esters of alkanoic acids, e.g. ethyl acetate, tetrahydrofuran, N,N'-dimethylformamide and the like.

The temperature of the condensation reaction may range from $-10°$ C. to $40°$ C. Generally the reaction is carried out at room temperature ($20°–25°$ C.), and for as long as needed for the reaction to be complete or substantially complete. Then the solvent is removed and the dipeptide is recovered by crystallization. The C-terminal ester is then removed by reaction with a slight excess of a suitable base (i.e. a methanolic solution of KOH) and the dipeptide (II) is obtained by further crystallization or freeze-drying, and employed as such in the process of the invention.

The following examples further illustrate the process for preparing representative compounds of formula (I), but they are not to be interpreted as a limitation to the scope of the invention.

EXAMPLE 1

Arginyl-arginyl-prolyl-tyrosyl-gem diamino-isoleucyl-(R,S)malonyl-leucine $$H-Arg-Arg-Pro-Tyr-NH-CH(CH(CH_3)CH_2CH_3)-NH-C(O)-CH(CH(CH_3)_2)-C(O)-OH$$

The synthesis is carried out using a Beckman 990 Synthesiser and a polyamide resin containing 1.0 meq of sarcosine per gram of resin. The resin is activated with ethylenediamine at 20° C. for 16 hours and then functionalized with (Fmoc-Nle)$_2$O.

The benzyl alcohol linkage agent is then attached to the amino-functionalised resin through amide bond formation using the activated derivative of formula (V) wherein TCP stands for 2,4,5-trichlorophenyl $$HO-CH_2-C_6H_4-O-CH_2-COOTCP \quad (V)$$

This last compound which is the acid-labile linkage agent between the resin and the peptide to be assembled, is then esterified with the residue HO-mLeu-D-Ile-NH$_2$ previously activated at the Leu carboxylic group.

Activation of said residue is carried out suspending the dipepetide HO-mLeu-D-Ile-NH$_2$ (490 mg, 1.8 mmol) in CH$_2$Cl$_2$ (3 ml) and adding HOBT (244 mg, 1.8 mmol) and DCCI (361 mg, 1.8 mmol) thereto.

The thus obtained solution is maintained at 0° C. for 30 minutes and then filtered; the solvent is removed under vacuum, the residue is redissolved in DMF and added directly into the reaction vessel containing the resin and contacted with NMM (183.6 mg, 1.8 mmol) and 4-dimethylaminopyridine (DMAP)(22 mg, 0.18 mmol). A total of 16 ml of DMF is employed.

The esterification reaction is carried out at 20° C. for 16 hours. The resin-bound peptide is then swollen in DMF/H$_2$O (3/1, v/v); TIB (774 mg, 1.8 mmol) dissolved in DMF is then added to the resin. After stirring for 60 minutes, the excess reactant is drained off and the resin is washed again with DMF/H$_2$O (3/1, v/v) before adding an additional portion of TIB (774 mg, 1.8 mmol). The mixture is stirred for 16 hours. After further washings with DMF/H$_2$O (3/1, v/v), the resin is washed with anhydrous DMF in order to remove even traces of water; the trifluoroacetic acid salt is then neutralized by washing with DMF (15×1 min.), 10% DIPEA in DMF (3×1 min.) and finally with DMF (10×1 min.).

Then the following compounds are sequentially added: [(Fmoc-Tyr-(Bu$^t$)]$_2$O (1648 mg, 1.8 mmol), (Fmoc-Pro)$_2$O (1214 mg, 1.8 mmol), [(Fmoc-Arg(Mtr)]$_2$O (2180 mg, 1.8 mmol) and [(Fmoc-Arg(Mtr)]$_2$O (2180 mg, 1.8 mmol), dissolved in 16 ml of DMF.

The acylation reaction is carried out by following the conventional synthetic cycle technique known in peptide synthesis.

The N-terminal arginine protecting group is then cleaved by washing twice with 20% piperidine in DMF for 3 and 7 minutes respectively, and the peptide $$H-[Arg^8(Mtr),Arg^9(Mtr),gIle^{12},(R,S)mLeu^{13}]NT^{8-13}$$

bound to the resin is thus obtained.

Amino acid analysis of the resin bound-peptide after acid hydrolysis with 6N HCl azeotropic mixture for 18 hours at 105° C., gave the following results:

Nle 1.61; Tyr 1.00; Pro 1.18; Arg 1.78.

Detachment of the peptide from the resin is performed by treating the resin (92 mg) with trifluoroacetic acid (TFA)(10 ml) containing 6% Thioanisole at 20° C. for 5 hours.

Then the solution is filtered, the solvent is removed under vacuum and the residue is recovered and freeze-dried.

The yield of the cleavage reaction, measured by amino acid analysis of the residue resin, is 95%.

Amino acid analysis of the thus obtained hexapeptide is as follows: Tyr 1.00; Pro 1.12; Arg 1.80.

The residue is taken up in water and the hexapeptide is purified by chromatography on a 70×0.9 cm column.

A Whatman CM-52 resin is employed using a linear gradient of 0.03–0.3M ammonium acetate (AcONH$_4$), pH 6.6 and flow rate 1.0 ml min$^{-1}$.

19.4 μmol of the compound of the title (46%) are obtained. HPLC and tlc analyses confirmed that the product, which shows the correct amino acid content: Tyr 1.00; Pro 0.96; Arg 2.01, is homogeneous.

The structure of the product is confirmed by NMR analysis.

Preparation of the starting material (A) Preparation of $$HCl.NH_2-CH(CH(CH_3)CH_2CH_3)-C(O)-NH_2 \quad (D)$$

Boc-D-Ile-OH (6.39 g, 27.48 mmol) and tetrahydrofuran (THF) (60 ml) are changed into a 250-ml reaction flask equipped with stirring means.

The solution is cooled to −15° C. and N-methylmorpholine (2.78 g, 27.48 mmol), isobutylchloroformate (3.75 g, 27.48 mmol) and, 3 minutes later, 30% NH$_4$OH (5 ml, 42.85 mmol) are sequentially added thereto while the reaction temperature is maintained lower than −10° C.

The thus obtained solution is allowed to stand at −15° C. for 30 minutes and at 20° C. for 60 minutes.

The reaction product is precipitated by the addition of water (1000 ml), recovered by filtration and dried under vacuum for 16 hours.

Cleavage of the tert-butoxycarbonyl (Boc) protecting group from the obtained product is achieved by treatment of the product with 4.8M HCl in ethyl acetate (20 ml) (AcOEt). After standing for 3 hours at room temperature (20°–25° C.), the solvent is evaporated off and the residue is recovered by filtration.

HCl.D-Ile-NH₂ (2.52 g, 15.12 mmol, 53%) is obtained with m.p. 247°-8° C. and $[\alpha]_D^{20} = -21.88°$ (c=1, H₂O)

(B) Preparation of HO-mLeu-D-Ile-NH₂

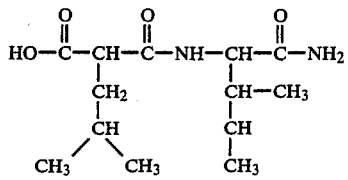

mLeu(OEt)OH (1.35 g, 7.2 mmol) is dissolved in CH₂Cl₂ (30 ml) and the solution is cooled to 0° C.

N-hydroxybenzotriazole (HOBT) (1.07 g, 7.92 mmol) in N,N'-dimethylformamide (DMF)(1 ml) and dicyclohexylcarbodiimide (DCC) (1.63 g, 7.92 mmol) are then added thereto.

The mixture is kept, under gentle stirring, at 0° C. for 30 minutes and at a temperature of about 20° C. for additional 30 minutes.

The reaction mixture is then filtered into a DMF solution (8 ml) containing HCl.D-Ile-NH₂ (0.6 g, 3.6 mmol) and NMM (0.36 g, 3.6 mmol).

The thus obtained mixture is stirred at 20° C. for 12 hours. The reaction solvent is then evaporated off to dryness, the obtained residue is taken up with AcOEt (100 ml) and washed with a 5% NaHCO₃ aqueous solution (30 ml), 0.1M HCl (30 ml) and then with a saturated NaCl aqueous solution (30 ml).

The organic phase is then separated from the obtained solution and dried over anhydrous MgSO₄. The solvent is evaporated off in vacuo and the residue is recovered by crystallization from AcOEt/petroleum ether (1/1, v/v) (100 ml).

The thus obtained product (1.0 g, 3.3 mmol) is dissolved in dioxane/H₂O (4/1, v/v) (40 ml) and 1M NaOH in dioxane/H₂O (1/1, v/v) (5 ml) is added thereto.

The reaction mixture is allowed to stand at 20° C. for 30 minutes. Then the solvent is evaporated off in vacuo, the aqueous phase is extracted with AcOEt (60 ml), the aqueous phase is acidified to pH 2 with concentrated HCl and finally extracted with AcOEt (100 ml).

This last organic phase is washed with water up to neutral pH and dried over MgSO₄.

The mixture is filtered and the solvent is removed under vacuum.

The oily residue thus obtained is taken up in dioxane (200 ml) and freeze-dried.

The compound HO-mLeu-D-Ile-NH₂ (0.820 g, 30 mmol, 83%) is obtained with m.p. 144°-7° C.

The compound structure has been confirmed by mass spectrometry and ¹H-NMR.

EXAMPLE 2

Synthesis of the hexapeptide

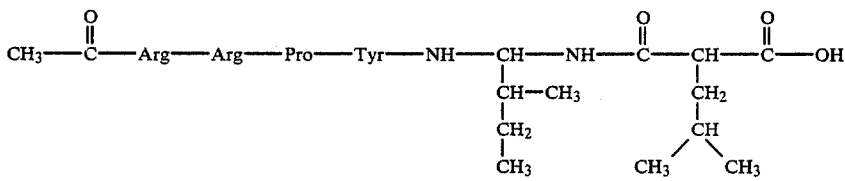

The synthesis is carried out as in foregoing example 1 up to the preparation of the hexapeptide

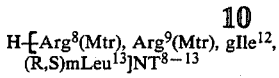

bound to the resin.

Then the N-terminal arginine is acetylated with acetic anhydride.

The reaction is performed by contacting the resin-bound hexapeptide with acetic anhydride (1.9 mmol) at 20° C. for 1 hour.

The peptide is then detached from the resin with a 96% yield.

Amino acid analysis of the cleaved hexapeptide Ac—(gIle¹², (R,S)mLeu¹³)-NT⁸⁻¹³ is as follows:

Tyr 1.00; Pro 1.20; Arg 1.98.

The hexapeptide is purified by reverse phase HPLC, using a Lichroprep®C-18 resin (25-40 μm) eluting with 0.02M AcONH₄ containing 24% CH₃CN and flow rate 7 ml min⁻¹. HPLC and tlc analyses showed that the product is homogeneous; amino acid content is as follows: Tyr 1.00; Pro 1.06; Arg 1.98. Purification yield is 41%.

We claim:

1. A retro-inverso hexapeptide neurotensin analog of the following general formula

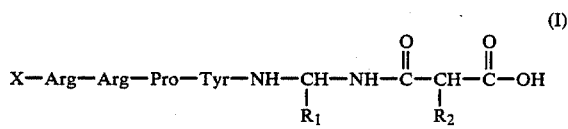

wherein:

X is a hydrogen atom or an acyl radical R₃—CO— wherein

R₃ is a straight or branched (C₁-C₇)alkyl group,

R₁ and R₂, each independently, represent the side-chain residue of the amino acid glycine (—H), alanine (—CH₃), valine

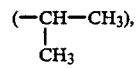

leucine

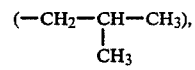

or isoleucine

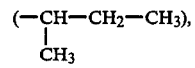

Arg is the abbreviated designation for arginine,
Pro is the abbreviated designation for proline, Tyr is the abbreviated designation for tyrosine, and the pharmaceutically acceptable salts, lower alkyl esters and amides thereof.

2. A retro-inverso hexapeptide neurotensin analog as in claim 1, wherein $R_1$ is the side-chain residue of isoleucine and $R_2$ is the side-chain residue of leucine.

3. A dipeptide of formula (II)

$$NH_2-\overset{O}{\underset{}{C}}-\underset{R_1}{CH}-NH-\overset{O}{\underset{}{C}}-\underset{R_2}{CH}-\overset{O}{\underset{}{C}}-OH \qquad (II)$$

wherein $R_1$ and $R_2$ are as defined in claim 1.

4. A pharmaceutical composition useful for the treatment of hypertension and related clinical conditions which comprises a therapeutically effective amount of a compound of claim 1 and a pharmaceutically acceptable carrier thereof.

5. A method of lowering blood pressure in mammals which comprises administering to a hypertensive mammal a therapeutically effective amount of a compound of claim 1.

* * * * *